United States Patent [19]

Markman

[11] Patent Number: 5,792,169
[45] Date of Patent: Aug. 11, 1998

[54] METHOD AND APPARATUS FOR FORMING MULTIPLE CAVITIES FOR PLACEMENT OF HAIR GRAFTS

[76] Inventor: Barry Stephen Markman, 5157 Jerom. Las Vegas, Nev. 89120

[21] Appl. No.: 561,018

[22] Filed: Nov. 21, 1995

Related U.S. Application Data

[63] Continuation-in-part of Ser. No. 395,455, Feb. 28, 1995.

[51] Int. Cl.⁶ .................................................. A61B 17/34
[52] U.S. Cl. .............................................. 606/186; 623/15
[58] Field of Search ................................ 606/184, 185, 606/186, 187; 623/15; 604/173

[56] References Cited

U.S. PATENT DOCUMENTS

| | | | |
|---|---|---|---|
| 3,998,230 | 12/1976 | Miller | 606/187 |
| 4,517,997 | 5/1985 | Forchetti | 623/15 |

*Primary Examiner*—Michael Buiz
*Assistant Examiner*—William Lewis

[57] ABSTRACT

A method and apparatus for forming multiple cavities in the tissue of a patient into which hair transplant grafts are placed is disclosed. The apparatus comprises interengaging plates. A first plate includes a number of downwardly extending spikes for extension through a number of downwardly extending hollow catheters of a second plate. The first and second plates are pressed together with the interengaging spikes and catheters penetrating the tissue. The first plate is removed, leaving cavities formed by the hollow catheters of the second plate. A third plate having downwardly extending hollow catheters filled with hair grafts is sleeved into or aligned with the catheters of the first plate. The hair grafts are pressed downward through the third plate, through the first plate, into the scalp, preferably by use of rods extending down from a fourth plate. The third plate may take the form of a rotatable circular wheel or replaceable cartridge which has bores therethrough for holding hair grafts, which is located between the first plate and the second plate.

13 Claims, 7 Drawing Sheets

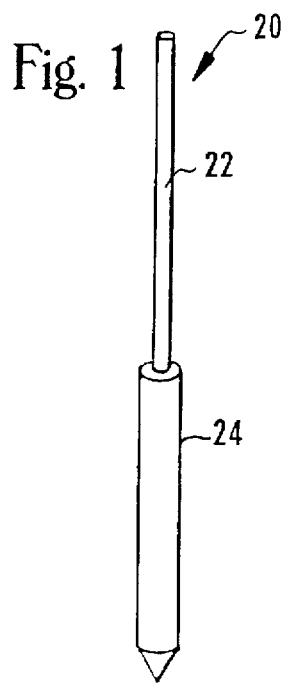
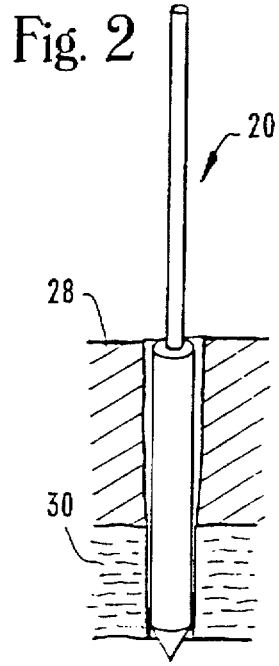
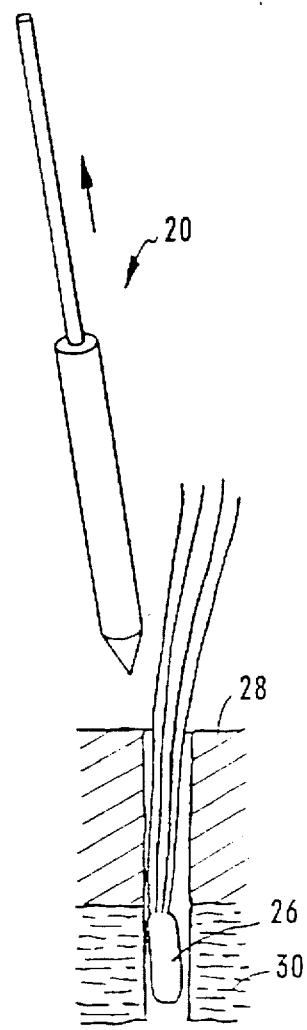
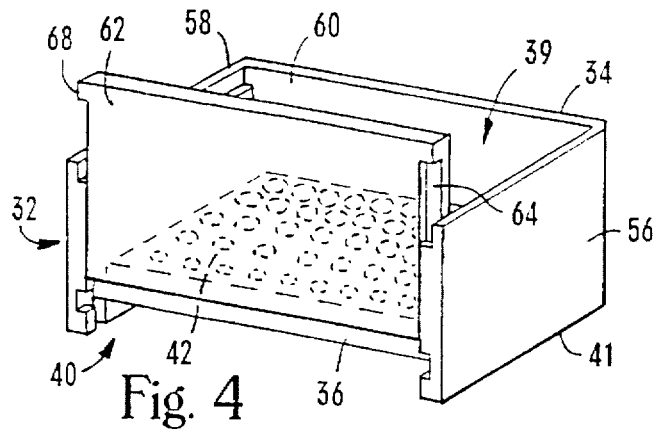
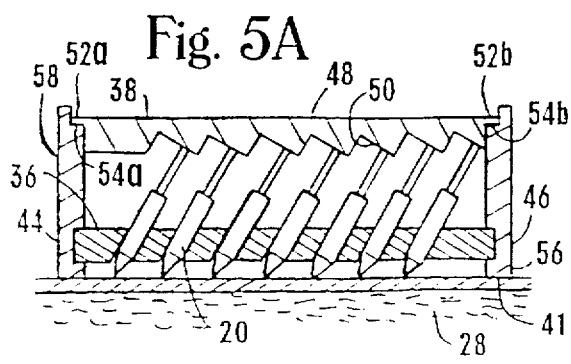
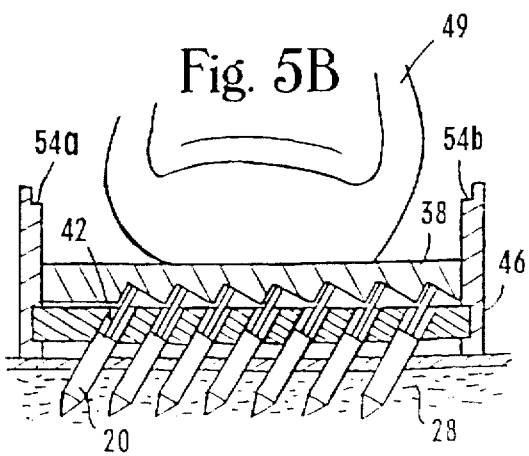

METHOD AND APPARATUS FOR FORMING MULTIPLE CAVITIES FOR PLACEMENT OF HAIR GRAFTS

RELATED APPLICATION DATA

This application is a continuation-in-part of U.S. patent application Ser. No. 08/395,455, filed Feb. 28, 1995, still pending.

FIELD OF THE INVENTION

The present invention relates to the placement of hair grafts. In particular, the invention is a method and device for forming a plurality of cavities in a predetermined pattern for positioning of hair grafts.

BACKGROUND OF THE INVENTION

Hair transplants have become commonplace over the last few years. In one of the newest technique of transplanting hair, small "grafts" of tissue containing only a few hairs are placed in sites on a recipient's scalp.

In particular, hair from other portions of the recipient are cut into very small cylindrical sections, or grafts. The recipients scalp is anesthetized, and then expanded by infusing saline into the scalp beneath the galeal layer. The surgeon inserts a needle-like dilator through the scalp, including the galeal layer, forming a cavity. The dilator is removed, and a donor graft is inserted into the cavity.

The success rate of this technique depends primarily upon whether the dilator succeeds in forming an cavity which extends below the galeal layer, and upon the time lapse between preparation and insertion of the graft.

New techniques in hair grafting require a large number, often 200 to 600, grafts to be placed during a single session. In the present technique, dilators are individually placed by hand. This is not only time consuming, but is inexact, since the surgeon places the dilators essentially randomly.

In order for the transplanted hair have a uniform look and proper coverage, however, the grafts must be arranged on the scalp in specific patterns. For example, numerous small grafts are often placed near the hairline, while larger grafts are placed less densely on the top and rear of the scalp.

A need exists for a method of easily forming cavities into which hair grafts are inserted and for controlling their location and number of dilators inserted across the entire scalp.

SUMMARY OF THE INVENTION

The present invention is a method and device for forming a number of cavities in the tissue of a patient into which hair grafts are inserted.

In one form of the present invention, a cartridge includes a four-sided, walled housing having open top and bottom ends. A template or guide is removably located in the housing, recessed from a bottom edge of the housing. A plurality of passageways are located through the guide for containing a plurality of dilators in a grid pattern therein.

The dilators are releasably retained in the passageways of the guide by friction between the dilators and the guide. Each dilator includes a lower or proximal probe portion for insertion into the scalp and an upper or distal grip portion by which the surgeon grasps the dilator. The distal grip portion is smaller in outer dimension than the probe portion.

The distal end of the dilators faces the top end of the housing, and the proximal end of the dilators faces the bottom end of the housing. A depressor is located over the open top end of the housing proximate the distal end of the dilators.

A surgeon places the cartridge on the patient's scalp with the bottom edge of the housing resting on the patient's head. The surgeon presses downwardly on the depressor, forcing the dilators downwardly out of the guide into the tissue of a patient. Once the dilators are inserted, the housing is removed from the scalp.

In a variation of this form of the present invention, the depressor is a plunger connected to an actuator. In this form of the invention, the housing of the cartridge is adapted to engage the triggering mechanism of an actuating mechanism, and triggering of the mechanism causes the actuator to depress the plunger, forcing the dilators from the guide into the tissue.

In other forms of the present invention, the housing is a cylindrical and rotatable with respect to a base member which adapted for insertion into a triggering mechanism. The housing includes a plurality of passages therein in which dilators are located. An actuating member passes from the base member through the housing to a plunger located proximate a first end of the dilators located in the passages. When a surgeon triggers the mechanism, one or more dilators are forced out of the passages into the tissue of a patient. The surgeon then rotates the housing with respect to the base, aligning another passage for actuation by the firing device.

In yet another form of the invention, the device for forming the cavities in the tissue comprises a female template having a number of downwardly depending guides with passages therethrough, along with a mating male template having a number of downwardly depending spikes. When engaging one another, the spikes of male template pass through the passages in the guides of the female template, forming a single template with downwardly extending "dilators."

In use, a surgeon presses the dilators of the combined male and female templates into the tissue of a patient. The surgeon removes the male template, leaving the female template in place. The surgeon then presses a third template having downwardly extending hollow guides each containing a hair graft into the female template. The surgeon presses the spikes of the male template through the guides of the third and female templates, pressing the hair grafts downwardly. Then the surgeon removes the templates, leaving the hair grafts positioned in the tissue.

In another version of the present invention, the device for creating apertures in the tissue and placing the hair grafts comprises four interengaging plates. An incision catheter plate comprises a base having a number of downwardly extending hollow catheters aligned with bores in the base. An incision needle plate comprises a base having a number of downwardly extending spikes for extension into the catheters of the incision catheter plate. A hair graft catheter plate comprises a base having a number of downwardly extending hollow catheters aligned with bores in the base. A hair graft needle plate comprises a base having a number of downwardly extending rods.

Posts extend upwardly from the incision catheter plate for engagement with bores in each of the other plates for aligned stacking of the plates.

In use, the user presses the incision needle plate and incision catheter plate together until the spikes extend just beyond the open end of the catheters. The user presses the plates downwardly so that the spikes/catheters extend into the tissue of a patient. The user removes the incision needle plate, leaving the catheters of the incision catheter plate located in the tissue.

The user presses the hair graft catheter plate (with hair grafts loaded into each catheter) downwardly until the catheters thereof are located in the catheters of the incision catheter plate. The user then presses the hair graft needle plate downwardly so that the rods thereof extend into the catheters of the hair graft catheter plate, thus pressing the hair grafts downwardly. The user then removes all of the plates, leaving the hair grafts in the tissue of the patient.

In another version of the present invention, the device for use in creating apertures and placing the hair grafts comprises a lower plate, upper plate, and at least one cartridge. Hollow catheters extend from the lower plate, and are aligned with bores passing therethrough. Spikes extend downwardly from the upper plate, which is movably mounted above the lower plate. The cartridge is located between the upper and lower plate. In a first form, the cartridge comprises a rotatable wheel having several sets of bores which are alignable with the catheters/spikes. In a second form, the cartridge comprises a small individual plate having a set of bores therein. Means are provided for aligning the bores in the cartridge(s) with the spikes catheters.

In use, a user presses the upper plate downwardly, extending the spikes thereof through empty bores in the cartridge and the catheters. The user then presses the entire device downwardly until the interengaging spikes/catheters extend into the tissue of the patient. The user then lifts up on the upper plate, and either inserts a loaded cartridge or rotates the cartridge, so that bores filled with hair grafts are aligned with the catheters. The user then presses the upper plate downwardly, pressing the hair grafts into the catheters. The user then removes the device, leaving the hair grafts in the tissue of the patient.

In this form of the invention, the user may preload large numbers of hair grafts into the cartridge(s), thereby allowing him to place large numbers of grafts in uninterrupted fashion.

Further objects, features, and advantages of the present invention over the prior art will become apparent from the detailed description of the drawings which follows, when considered with the attached figures.

BRIEF DESCRIPTION OF THE DRAWINGS

FIG. 1 is a perspective view of a single dilator for use in the present method;

FIG. 2 is a perspective view of the dilator of FIG. 1 inserted into the scalp of a patient;

FIG. 3 is a perspective view of the dilator of FIG. 2 being removed from the scalp, and being replaced by a hair graft;

FIG. 4 is a partial perspective view of a manually operated multiple-dilator placing cartridge in accordance with the present invention; and FIG. 5a is a front end view of the cartridge of FIG. 4 with a depressor thereof in a first, retracted position;

FIG. 5b is a front end view of the cartridge of FIG. 4 with a depressor thereof in a second, depressed position;

DETAILED DESCRIPTION OF THE PREFERRED EMBODIMENT

Figure 6:
FIG. 6 is a perspective view of a patient's scalp, illustrating that certain portions of the scalp require differing hair graft sizes and densities, and thus differing sized dilators and dilator insertion points.

The present invention involves methods and devices for simultaneously forming cavities in the tissue of a patient into which hair grafts are located. In particular, the methods involve pressing dilating elements into the tissue of a patient to form cavities in which hair grafts are placed.

FIG. 1 illustrates a dilator 20 for use in some of the methods and devices of the present invention. In general, the dilator 20 comprises a distal handle portion or end 22 and a proximal probe portion or end 24. Preferably, the very end of the handle portion is blunt, and the very end of the probe portion is pointed. As illustrated in FIG. 2, the dilator 20 is inserted in the tissue of a patient, normally the scalp, for creating an cavity into which a hair graft 26 is inserted. In a first method in accordance with the present invention, a number of dilators 20 are simultaneously located in the tissue when a surgeon manually presses on a dilator-engaging depressor 38, pushing a number of dilators through a guide 36 into the scalp, as illustrated in FIGS. 5a and 5b.

Figure 7:
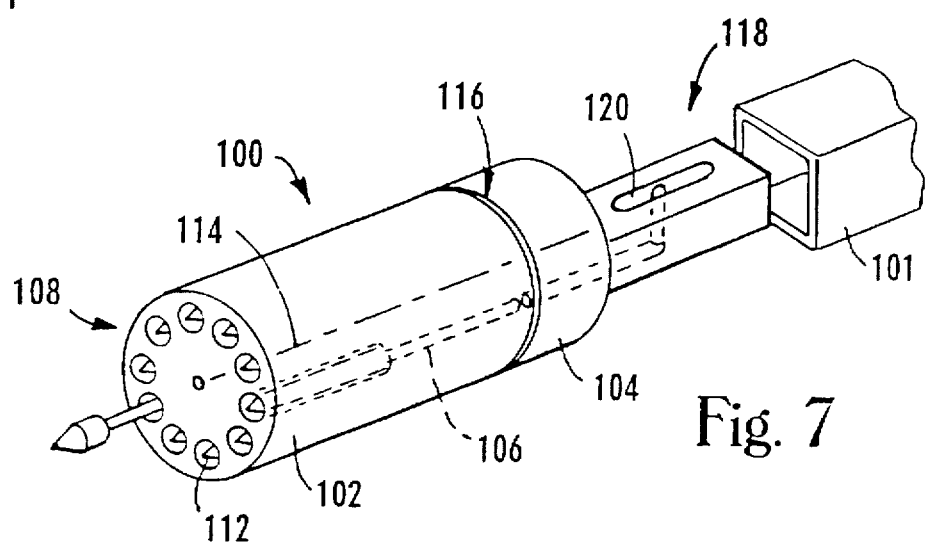
FIG. 7 is a perspective view of a second embodiment of the present invention, illustrating an automated revolving single-shot dilator cartridge.

In a second method, a series of single dilators 20 are inserted into a scalp upon actuation of a gun or other remote triggering device, via the cartridge illustrated in FIG. 7. In a third method, multiple dilators 20 are inserted into the scalp when a surgeon actuates a gun, via the cartridge illustrated in FIG. 8.

Figure 9:
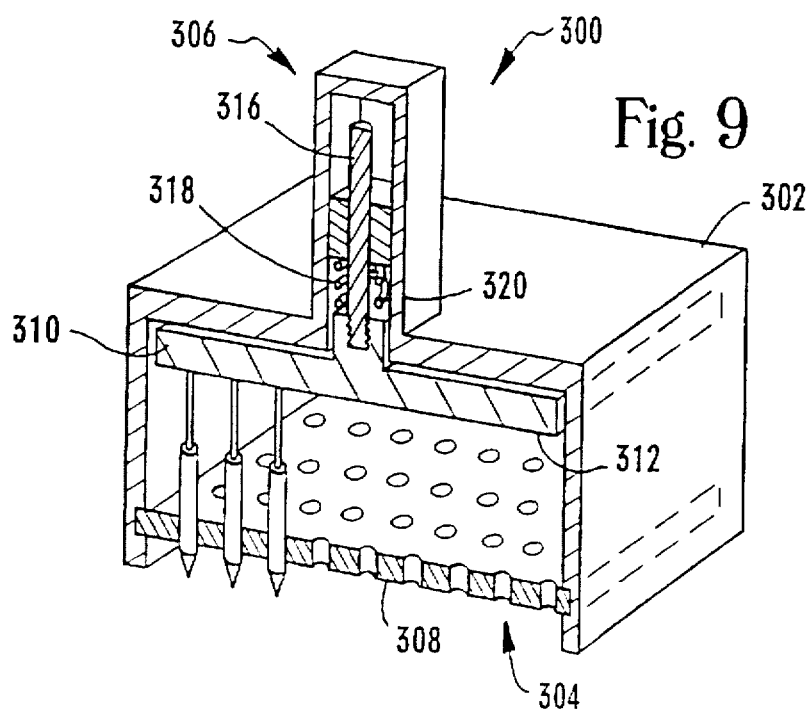
FIG. 9 is a top view of a fourth embodiment of the present invention illustrating an automatically operated dilator insertion cartridge.

In a fourth method, a number of dilators 20 are simultaneously inserted into the scalp when a surgeon triggers an actuating mechanism connected to the cartridge 300 illustrated in FIG. 9.

Figure 11:
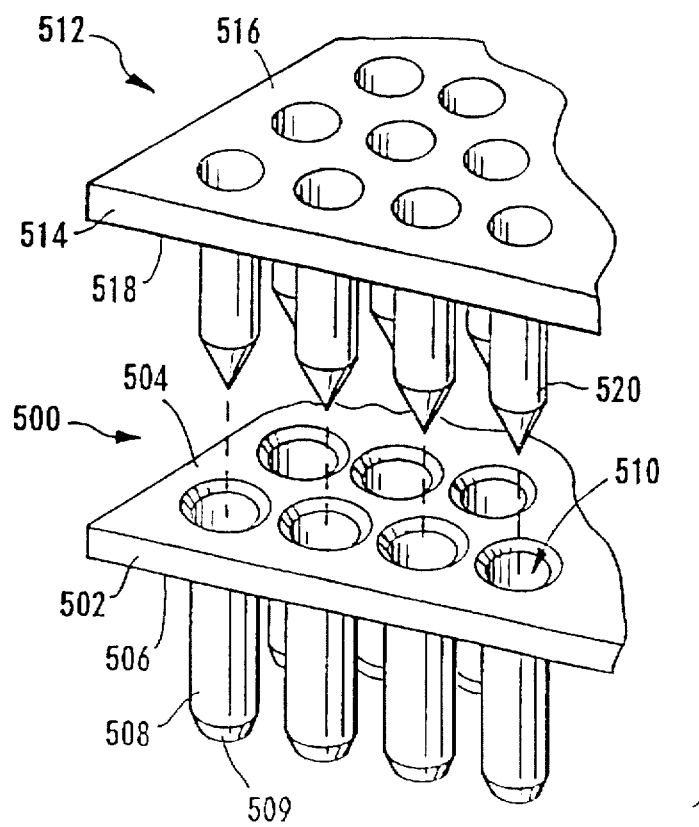
FIG. 11 is a partial perspective view of a male and a female template of a fifth form of the invention.
Figure 12:
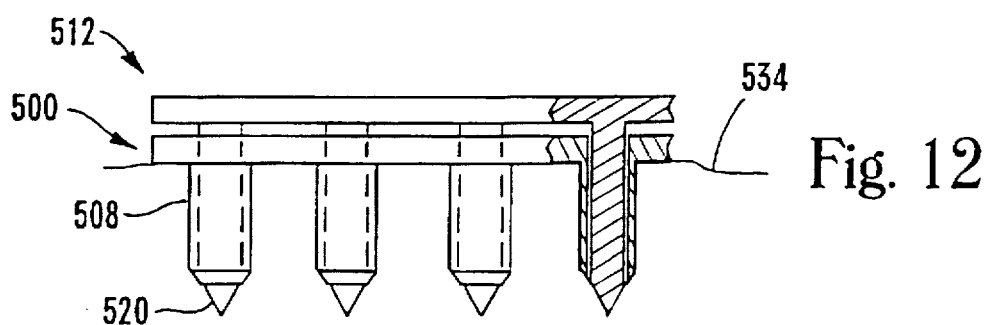
FIG. 12 is a cross-sectional side view of the male and female template of FIG. 11 shown engaging one-another and pressed into the tissue of a patient.
Figure 13:
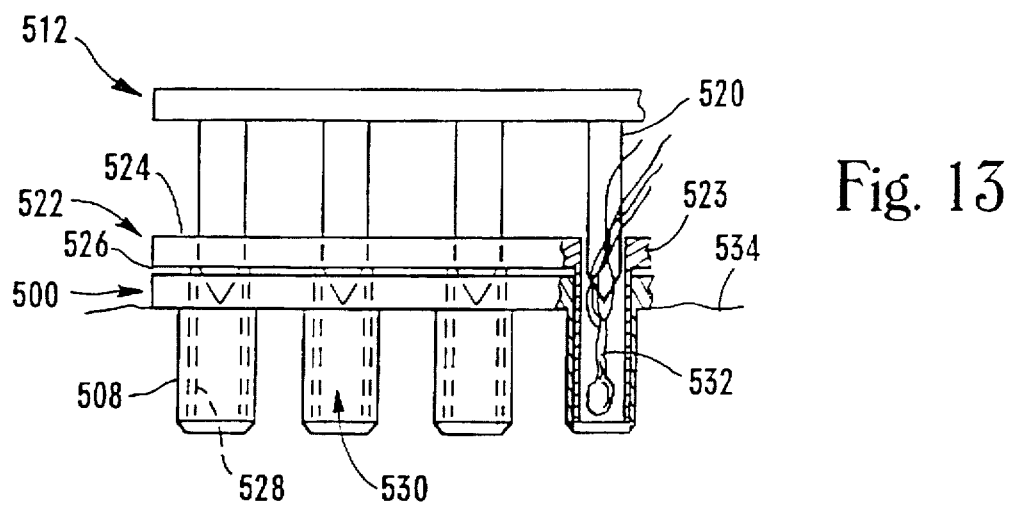
FIG. 13 is a cross-sectional side view of a third template engaging the female template of FIG. 11, with the male template engaging the third template.

In a fifth method, the interengaging templates illustrated in FIGS. 11–13, which include downwardly depending dilating spikes and guides, are used to penetrate the tissue and form open cavities into which hair grafts are inserted.

More particularly, and referring again to FIGS. 1–3, in a first form, the dilators 20 of the present invention are preferably cylindrical in shape, and about 2 cm long from end to end. In particular, the handle portion 22 is about 1 cm long and about 0.5 mm in diameter. The probe portion 24 is about 1 cm long and has a larger diameter than the handle portion, being about 1 mm in diameter. The dilator 20 tapers to a sharp point at the very end of the probe portion for piercing and penetrating tissue, over about the last 0.25 cm of the dilator.

Most importantly, because the handle portion 22 of the dilator 20 has a smaller outer dimension that the probe portion 24, a cavity which is large enough to accept a hair graft is formed when the dilator is inserted into the scalp, and yet a sufficient distance between the handles exists to allow the surgeon to grasp them and work between them.

FIGS. 1–3 illustrate, in overview form, use of a single dilator 20 to facilitate hair graft 26 insertion. First, the dilator 20 is pressed downwardly into the scalp 28 into the galeal layer 30. Penetration of the scalp 28 is facilitated by the tapered end of the dilator 20.

Once inserted into the tissue of a patient, the enlarged probe portion 24 expands the surrounding tissue, as illustrated in FIG. 2. After insertion, the surgeon removes the dilator 20 as illustrated in FIG. 3, leaving an cavity into which the surgeon inserts the hair graft 26. The resiliency of the tissue ultimately causes the tissue around the hair plug 26 to close, securing the graft in place.

FIG. 4 illustrates a manually operated device for use in placing multiple dilators 20 in accordance with a first method of the present invention. In accordance with this method, by manual effort, a surgeon simultaneously places a number of dilators 20 in a predetermined arrangement. The device for accomplishing the method is a cartridge 32 which comprises outer support means in the form of a housing 34 having the form of a contiguous upright wall, a dilator guide 36, and a depressor 38 (see FIGS. 5A and 5B).

The housing 34 of the cartridge 32 is preferably square or rectangular in shape. The particular size, in inner dimension and thickness, varies on the number of dilators to be placed and their size. When four-sided, the housing 34 has a first side 56, a second side 58, a third side 60, and a fourth side 62, and an open top end 39 and bottom end 40.

Preferably, the first, second and third sides 56,58,60 are rigidly connected, forming a "C"-shaped member. The fourth side 62 is movably or removably connected to the other sides. In particular, the edges of the first and second sides 56,58 which engage the fourth side 62 include a "C"-shaped channel. The fourth side 62 has inwardly facing tabs 64,66 (66 not visible) on opposing edges which slide in the channels of the first and second sides 56,58. The fourth side 62, as illustrated in FIG. 4, is thus detachably connected to the first and second sides 56,58.

Preferably, a stop 68 in the form of a solid member covering the top end of the channels 64,66, limits downward movement of the fourth side 62 on the first and second sides 56,56. When connected to the first and second sides, the fourth side completes the contiguous wall comprising the housing 34.

Each of the sides is made of plastic, or a similar durable and sterilizable material. When made of plastic, the first, second, and third sides 56,58,60 can be molded as a single piece.

Dilator guide means in the form of a guide or template 36 are located in the cartridge, recessed a short distance up from a bottom edge 41 of the housing 34 on the interior thereof. The particular recess distance is chosen so that when the cartridge 32 is placed on the scalp, the tips of the dilators 20 located in the cartridge 32 are proximate the scalp, as illustrated in FIG. 5a.

The dilator guide 36 is a rectangular member having first and second ends or sides which engage a first groove 44 in the first side 56 of the wall 34, and a second groove 46 in the opposite second side 58 of the wall. The grooves 44,46 are recessed areas in each of these two sides 56,58 having approximately the same height as the thickness of the guide. The engagement of the guide 36 with the grooves 44,46 supports the guide in the housing 34 above the bottom end thereof.

The guide 36 is preferably made of a slightly flexible material, such as rubber, and includes a plurality of passages 42 therethrough. As illustrated in FIG. 4, the passages pass through the guide 36 at about a 30 degree angle with respect to vertical. The passages 42 can be arranged in a variety of patterns, depending on the particular dilator placement pattern desired.

Each passage 42 is sized to accept a dilator. When the dilators 20 have the shape described above, the passage 42 is circular in shape, having approximately the same diameter as the larger probe portion of the dilator 20.

Stop means retain the dilators in the guide 36 in a first position. Preferably, the stop means comprises friction between the dilators and the guide 36. In particular, the size of the passage 42 and the type of material from which the guide 36 is selected so that a dilator 20 placed in a passage is retained therein unless pushed through by an outside force. As illustrated in FIG. 4, the passage size varies when the dilator size varies, such that an individual cartridge can contain a guide having passages of differing sizes.

The depressor 38 is located near the top end 39 of the housing 34, and has a top surface 48, bottom surface 50, and two opposing edges each having an outwardly extending tab 52a,b thereon. The top surface 48 is preferably flat and smooth for engagement with the thumb 49 or finger of a surgeon. The bottom surface 50 is "stepped" providing a number of individual surfaces arranged parallel to the end of each dilator.

The tabs 52a,b are thin members extending outwardly along opposite edges of the depressor. The tabs 52a,b each engage a corresponding ledge 54a,b on the first and second sides 56,58 of the housing, acting as means for supporting the depressor 38 above or at the ends of the dilators 20 in a first raised position. When a surgeon presses upon the depressor, however, the tabs 52a,b break off, allowing the depressor 38 to move downwardly within the wall 34 of the cartridge 32.

In the first method, a surgeon uses the cartridge 32 of the present invention to simultaneously place a number of dilators 20. First, the surgeon lifts the fourth side 62 upwardly, exposing the interior portion of the cartridge 32. The surgeon presses a dilator guide 36 into the cartridge, the particular guide chosen to have the desired dilator insertion pattern required for that portion of the scalp in which hair grafts are to be inserted.

FIG. 6 illustrates in overview schematic form how hair grafts 26 of different sizes are placed in differing regions of the scalp. Along the normal hair line, many small grafts are inserted. In the central or interior portion of the scalp, larger hair grafts are inserted. Thus, not only does the "density" of the dilators being placed need to vary, but their size often must vary as well.

Once a guide 36 having the desired dilator pattern (in both size and density) is chosen, it is inserted into the cartridge, and the fourth side 62 is pressed downwardly. When relocating the fourth side, the channels 64,66 slide along and engage the edges of the first and second sides 56,58, until the stops 68 prevent further downward movement of the side.

Preferably, the appropriately sized dilators 20 are already inserted into the passages 42 in the guide 36 when the guide is inserted. If not, the surgeon inserts dilators into the passages 42.

The surgeon then places the cartridge 32 on the scalp in the desired position, as illustrated in FIG. 5a. In this position, the dilators 20 are located proximate the scalp.

The surgeon then presses downwardly on the depressor 38. Pressure on the depressor breaks off the tabs 52a,b on the edges of the depressor, allowing the depressor to slip downwardly past the ledges 54a,b on the first and second sides 56,58 of the wall 34.

The depressor, which engages the handle portions 22 of the dilators 20, presses them downwardly into the scalp. Eventually, further movement of the depressor 38 is prevented by its contact with the guide, as illustrated in FIG. 5b.

The cartridge 32 is then removed, leaving the dilators in place in the scalp. The cartridge 32 is easily removed without disrupting the dilators 20 because the dilators no longer engage the guide because the small diameter handle portion 22 of each dilator 20 is all that remains in the larger passages 42 of the guide. Then, as illustrated in FIGS. 2 and 3, the surgeon removes the dilators and inserts hair grafts 26 in their place, completing the transplant process.

Preferably, the range of movement of the depressor 38 against the dilators 20 equals the distance the dilators 20 must be pressed into the scalp for optimum hair graft insertion. In the case where the dilators 20 initially just contact the tissue when the cartridge is set on the patient, this distance is normally about 7 mm. Thus, the depressor's 38 range of movement against the dilators is about 7 mm.

The cartridge 32 of the present invention is reusable. In particular, the surgeon removes the old used depressor 38 from the cartridge and replaces it with a new one having intact tabs 52a,b. When a new depressor 38 is installed, it is again supported by the tabs 52a,b the ledges 54a,b in a raised position.

The surgeon then either inserts new dilators 20 into the passages 42 of the guide, or replaces the guide 36 in the cartridge with a different one if a different dilator insertion pattern is desired.

The above description represents a preferred embodiment of the present invention. However, many variations to the method and device are possible without deviating from the scope of the invention.

For example, the cartridge 32 can have any of a variety of shapes and sizes. Further, the guides can have a variety of sized and spaced dilator accepting passages.

As a further aspect of the present invention, the guide may actually comprise a number of individual elements which are arranged together to form a single grid or element in the cartridge. In this fashion, the guide may be "customized" using only a few guides having fixed patterns. For example, the guides may comprise elongate members having a single row of passages therein, such that when a number of guides are placed together, a grid having numerous rows of differently spaced and sized passages results.

While it is desirable that the passages pre-formed in the guide, the guide may be made of a pliable material, whereby the surgeon can form the passages simply by pressing dilators into the guide in any desired pattern.

Further, while the passages in which the dilators are located are shown in FIGS. 4, 5a, and 5b as being tilted at a 30 degree angle with respect to the horizontal, the passages can have any orientation. For example, and as illustrated in FIG. 9, the passages can pass vertically through the guide. Alternatively, the passages can pass at an angle of 5, 10, or 45 or more degrees through the guide. When the angle at which the passages pass through the guide is different, the bottom surface 50 of the depressor is reconfigured so that the depressor engages each dilator at a right angle.

As described above, preferably the depressor engages the distal end 22 of the dilators 20 at a right angle. In an alternate form of the present invention, the depressor moves parallel to the direction of dilator movement through the guide. In particular, the depressor may be located on a track in the housing by which the depressor moves downwardly against the dilators at the same angle as the dilators extend through the guide.

A variety of means for selectively attaching the guides to the cartridge other than the engagement with the grooves described above are available. For example, the guide may snap into place or be press-fit into the housing, be held in place by spring-loaded pins which pass through the cartridge wall into the guide, or simply be supported by a ledge extending inwardly from the wall. Also, a variety of means for selectively attaching and detaching the fourth side to access the guides are possible.

Also, the guide may actually comprise a portion of the housing instead of a separate element. For example, the guide may comprise a molded section of plastic having passages or the like therethrough which is directly a part of the outer wall.

As described above, the stop means preferably comprises friction between the dilators and the guide. In this form of the invention, the guide is preferably constructed of rubber or a similar "stretchable" and high-friction material. The guide, however, may be constructed of plastic or a similar rigid material, with each passage lined with rubber or a similar material.

Also, the stop means for retaining the dilators in the template may comprise something other than the friction between the dilators and the guide. For example, a thin pierceable member such as a plastic sheet may be located over the open end of the housing. Alternatively, a removable panel may be located across the open end of the housing, the panel removed when the housing is placed on the scalp, there by allowing the dilators to be pressed into the scalp.

A second form of the present invention is illustrated in FIG. 7. FIG. 7 illustrates a cartridge 100 for use with an automated gun 101 or other remote automatic triggering or firing device of the type commonly used and found in hospitals and medical offices. Such mechanisms are commonly used to place items such as tissue staples.

In general, the cartridge. 100 comprises a tubular housing 102 rotatably connected to a base 104. An actuator 106 passes through the base 104 and into the housing 102 for pressing a dilator 20 therein out of the housing and into the scalp of a patient.

The housing 100 is cylindrical in shape, having a first end 108 and second end 110. The first end of the housing 108 is enclosed, while the second end 110 is open.

The housing 100 is hollow, except for a number of tubes or passages 112 extending inwardly from the first end 108. Each tube 112 has a diameter slightly greater than that of a dilator, and having a slightly longer length. Preferably, the tubes 112 are spacedly located about the outer periphery of the housing 102, and are open at both ends.

An axle 114 passes from the first end of the housing 102 to the base 104. The axle 114 passes along the centerline of the housing 102, allowing the housing 102 to rotate.

The base 104 has a first end 116 for mating engagement with the second end of the housing 102. The first end 116 of the base is thus circular in shape, comprising an outer wall and inner hollow interior space.

The base 104 includes a second end 118 which is adapted for mating engagement with a triggering device or gun 101. In the embodiment illustrated, the second end 118 has a generally rectangular shape.

An aperture 120 is located in one surface of the second end 118 of the base 104, forming a passage into the interior of the base. The actuator 106 is generally "L"-shaped, extending from the aperture through the base and into the housing 102. A first end of the actuator 106 extends upwardly to the aperture 120 for engagement by a trigger mechanism in the gun 101. A second end of the actuator 106 is located adjacent the end of one of the tubes 112.

Stop means releasably retain the dilators 20 in the tubes 112. The stop means preferably comprises friction caused by a slight interference fit between the dilator and the housing.

In use, a dilator 20 is placed in each of the tubes 112, with the tapered point facing outwardly. The base 104 of the cartridge 100 is located in a gun 101, and one of the tubes 112 is aligned with the second end of the actuator 106.

The surgeon actuates the gun 101, moving the actuator 106 towards the first end of the housing. The second end of the actuator 106 engages the end of the dilator 20 in the aligned tube, pressing the dilator through the tube and into the scalp. The surgeon lifts the gun 101 upwardly so that the housing 102 clears the end of the dilator, and proceeds to place the next dilator.

A surgeon places the next dilator by rotating the housing 102 with respect to the base 104, until the second end of the actuator 106 is aligned with another tube containing a dilator. The gun is again triggered, with the next dilator forced into the scalp.

In this form of the invention, the tube 112 holding the dilator 20 is located close to the outer edge of the housing 102, so that the next dilator can be placed very close to the last. Further, the range of movement of the actuator 106 is chosen so that the dilator 20 is pressed the appropriate distance into the scalp.

In this embodiment, the stop means may comprise a separate element such as a rubbery gasket through which the dilator extends, or a membrane or plate extending across the open end of the tubes which is either pierceable or movable when the dilators are depressed into the scalp.

Figure 8:
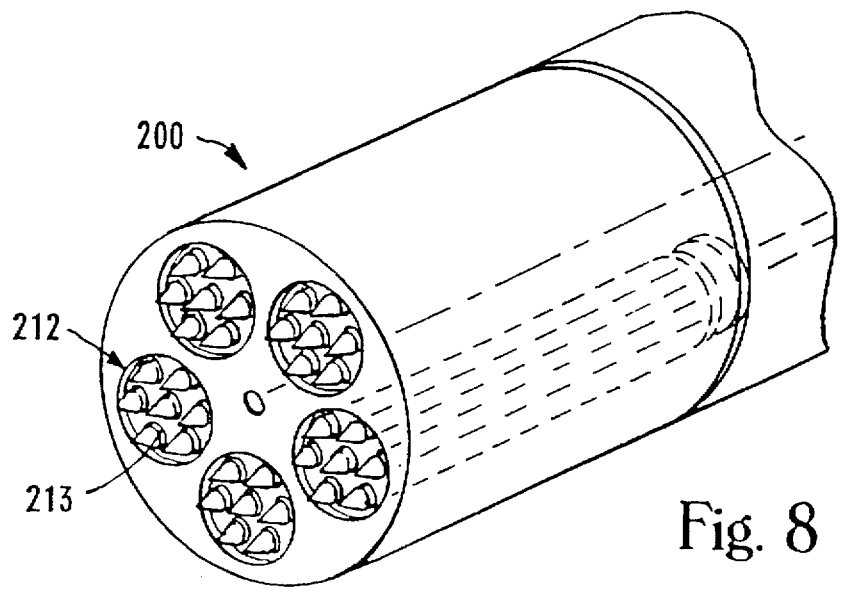
FIG. 8 is a perspective view of a third embodiment of the present invention, illustrating an automated rotating multiple shot dilator cartridge.

Further, the tubes or passages in which the dilators are located can be arranged in a variety of configurations. A third embodiment device of the present is illustrated in FIG. 8. In this embodiment, several dilators are placed in the scalp automatically when a surgeon operates a gun.

In particular, this cartridge 200 is nearly identical to that described above, except the tubes 212 in a housing 202 thereof are configured to receive multiple dilators 20. In the embodiment illustrated, each tube 212 is sized to receive seven dilators. The tube 212 thus includes eight distinct tubes or conduits 213, each of which holds a single dilator. Again, each end of each tube 212, and each passage 213 therein, is open.

In use, when a surgeon actuates the gun or automated firing device, the actuator presses all of the dilators in a tube 212 into the scalp. In the configuration illustrated, all eight dilators in the passages in a single tube are pressed into the scalp.

It is possible to have a wide variety of numbers of tubes and passages therein, for placing a different number of dilators. Further, the passages can be arranged in a wide variety of configurations, whereby the multiple dilators are placed in the scalp in a specific configuration.

FIG. 9 illustrates a fourth embodiment device of the present invention. In particular, this variation of the device if similar to that illustrated in FIG. 4, except that it is automated.

In this form of the invention, a cartridge 300 includes a housing 302 with a first bottom open end 304 and second gun-engaging end 306. A dilator guide 308 and depressor 310 are located inside of the housing 302.

The second end 306 of the housing 302 is shaped for engagement with the end of a triggering device, such as a spring-loaded or air-powered gun. In the form illustrated, the second end 306 is an elongate, somewhat rectangular shaped member.

The remainder of the housing 302 is box-shaped, except that the first end 304 is open. Similar to the cartridge 32 illustrated in FIGS. 4, 5a and 5b, a removable dilator guide 308 is located within the housing, recessed a short distance from the open first end 304.

Preferably, a surgeon can open and close one side of the housing 302 to access the guide 308, similar to the manner described above in the first embodiment.

The depressor 310 is located between the guide 308 (at the end of the dilators therein) and the second end 306 of the housing 302. The depressor 310 has a perimeter shape which matches the inside shape of the housing 302, to be freely moveable between a first retracted position and a second depressed position.

A bottom surface 312 of the depressor 310 is adapted to press on the dilators at a right angle, as discussed above in more detail. Preferably, the depressor 310 is connected to an actuator 316 which extends into the second end 306 of the housing for engagement with the gun.

Means for biasing the depressor 310 in the form of a pair of springs 318,320 maintain the depressor 310 in a normally retracted position. The springs 318,320 are chosen so that upon firing of the gun, the actuator 316 moves against the spring force, pressing the actuator downwardly against the dilators.

In use, a surgeon inserts a loaded dilator guide 308 into the housing 302 of the cartridge. Once loaded, the surgeon inserts the cartridge 300 into a gun. The surgeon then places the open end 304 of the cartridge 300 against the scalp of a patient in the desired location.

The surgeon triggers the gun, effectuating movement of the actuator 316 and pressing the depressor downwardly against the dilators and the opposing spring force. The dilators are pressed through the passages in the guide 308 and into the scalp. Once the dilators are placed, the springs 318,320 bias the depressor back upwardly to the retracted state, when a new loaded dilator guide can be inserted into the cartridge.

In accordance with this method, numerous dilators are simultaneously placed into the scalp using an automated machine. Once again, the particular location of the dilators is effectuated by choosing a guide having a specific configuration of dilator-holding conduits.

Figure 10:
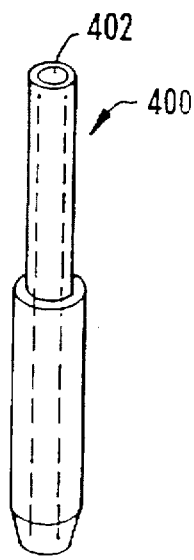
FIG. 10 illustrates a second form of dilator for use in the methods and devices of the present invention.

While it is preferred that the dilator illustrated in FIGS. 1-3 be used in the methods and devices of the present invention, other configurations of dilators can be used. For example, FIG. 10 illustrates a second form of dilator 400 for use in the methods and apparatus of the present invention. The dilator 400 is similar to that described above, except that it has a hollow passageway 402 along the centerline thereof. This dilator 400 has the effect of coring a section of tissue from the patient when the dilator is inserted and then removed.

FIGS. 11-13 illustrate a fifth embodiment of the present invention. In this embodiment of the present invention, the device for simultaneously placing dilators are interengaging plates or templates, with the dilators comprising a series of spikes on one of the templates. In particular, a first or female template 500 comprises a thin base member 502 having a top surface 504 and a bottom surface 506. A number of cylindrically shaped guides 508 depend downwardly from the bottom surface 506 of the template, each having a tapered or bevelled distal end 509. Each guide 508 has a length nearly equal to the depth the hair grafts must be placed into the tissue of the patient to maximize graft survival.

A passage 510 extends through the top surface 504 of the template down through each of the guides 508. The location of each of the guides 508 on the template 500 matches the spacing of later to be placed hair grafts 532.

A second or male template 512 comprises a thin base member 514 having a top surface 516 and bottom surface 518. A number of spikes or probes 520 extend downwardly from the bottom surface 518 of the template.

Preferably, the spikes 520 are longer than the passages 510 through the female template 500, and have a smaller outside diameter than the diameter of the passages 510 through the guides 508 and passages through the guides of a third template described below. The spikes 520 have a distal end which tapers to a point. The spikes 520 are arranged in the same pattern as the guides 508 on the female template.

As illustrated in FIG. 13, a third template 522 comprises a base plate 523 having a top surface 524 and bottom surface 526. A number of cylindrical guides 528 depend downwardly from the bottom surface 526 of the template. A passage 530 extends through the template 522 and each of the guides 528. Preferably, the outer dimension of each of the guides 528 is smaller than the size of the passage 510 of the female template 500. The guides 508 are arranged in the same pattern as the guides 508 in the female template 550, for mating engagement therewith.

In use, as illustrated in FIGS. 12 and 13, a surgeon presses the male template 512 into the female template 500. In particular, the surgeon aligns the spikes 520 of the male template with the passages 510 through the guides 508 in the female template 500. The surgeon presses the two templates 500,512 together until the bottom surface 518 of the male template 512 engages the top surface 504 of the female template. When engaging one another, the spikes 520 and guides 508 form "dilators" for placement in the tissue 534 of the patient. The surgeon places the combination on the scalp of the patient and presses downwardly until the bottom surface 506 of the female template 500 contacts the scalp, preventing further movement. The surgeon then pulls the male template 512 from the female template 500, leaving the female template in place.

When the female template 500 is in place, the passages 510 therethrough form cavities in the tissue of the patient into which hair grafts 532 may be inserted. In particular, the surgeon or an assistant places hair grafts 532 into each of the passages 530 of the third template 522, and then the surgeon presses the third template into engagement with the female template 500 which is engaging the patient.

When the surgeon presses the third template 522 into the female template 500, each hair graft 532 is effectively positioned in the tissue of the patient. Preferably, the surgeon then presses the male template 512 into the other two templates, whereby the spikes 520 engage the hair grafts 532 and push them into the bottom of the formed cavities. The surgeon then removes all of the templates, leaving the hair grafts 532 in place in the tissue of the patient.

In the above-described device, the templates may comprise substantially rigid members made of plastic or similar material. Preferably, however, so that the device can conform to the varying shape of the patient, the base of each template is constructed of a slightly flexible material, such as a rubber or flexible plastic. The spikes and guides, however, is preferably constructed of a rigid material which easily penetrates tissue.

Further, the size and location of the guides and corresponding spikes may vary. For example, the guides and spikes may be located on their respective bases in a variety of patterns for use in positioning hair graft in the same variety of patterns on the scalp. Also, the guides, and thus the matching spikes, may vary in size, both between different template, and even on the same template, depending on the size of hair graft to be implanted.

FIGS. 14a-d and 15-17 illustrate a sixth embodiment of the present invention. The sixth embodiment of the invention is similar to the last embodiment, except that four plates (instead of three) are preferably utilized for creation of cavities in tissue and placement of hair grafts.

This form of the invention comprises a incision catheter plate 602, incision needle plate 604, hair graft catheter plate 606, and hair graft needle plate 608.

Figure 14:
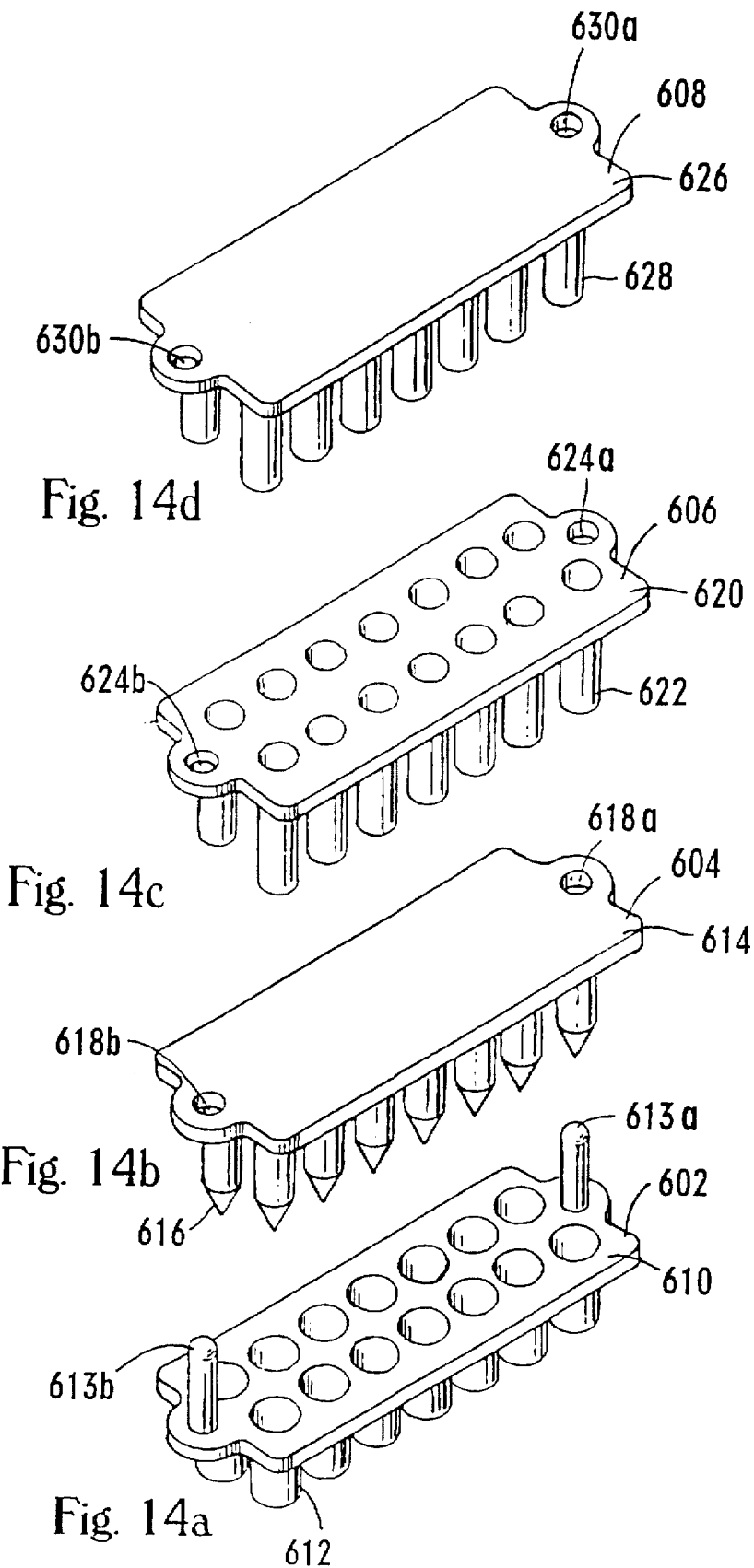
FIG. 14a is a perspective view of an incision catheter plate of a sixth form of the present invention.
FIG. 14b is a perspective view of an incision needle plate of a sixth form of the present invention.
FIG. 14c is a perspective view of a hair graft catheter plate of a sixth form of the present invention.
FIG. 14d is a perspective view of a hair graft needle plate of a sixth form of the present invention.

FIG. 14a illustrates the incision catheter plate 602. This plate 602 comprises a base 610 having a number of hollow catheters 612 extending downwardly therefrom. Each catheter 612 is hollow and aligned with a passageway or bore passing through the base 610.

Means for aligning the plates are provided. Preferably, the means include a guide post 613a,b extending upwardly from the base 610 of the plate 602 at each end thereof. In particular, the each post 613a,b preferably rises upwardly from the base 610 about 22-30 mm from a small extension of the base 610. As illustrated, the posts 613a,b are cylindrical in shape, having rounded top ends.

FIG. 14b illustrates the incision needle incision plate 604. The plate 604 comprises a base 614 having a number of spikes 616 extending downwardly therefrom. Preferably, the base 614 has approximately the same dimensions as the base 610 of the incision catheter plate 602. The spikes 616 are arranged on the bottom of the plate 604 in the same pattern and position as the catheters 612 of the incision catheter plate 602, whereby a user may align the spikes 616 with the catheters 612 and press the spikes into engagement with the catheters. Each spike 616 is preferably a cylindrical member which near the free end thereof tapers to a sharp point.

A bore 618a,b is located in the base 614 of the incision needle plate 604 at an extension of each end of the base. The bores 618a,b are positioned in the plate 614 for alignment with the posts 613a,b rising upwardly from the incision catheter plate 602.

Figure 15:
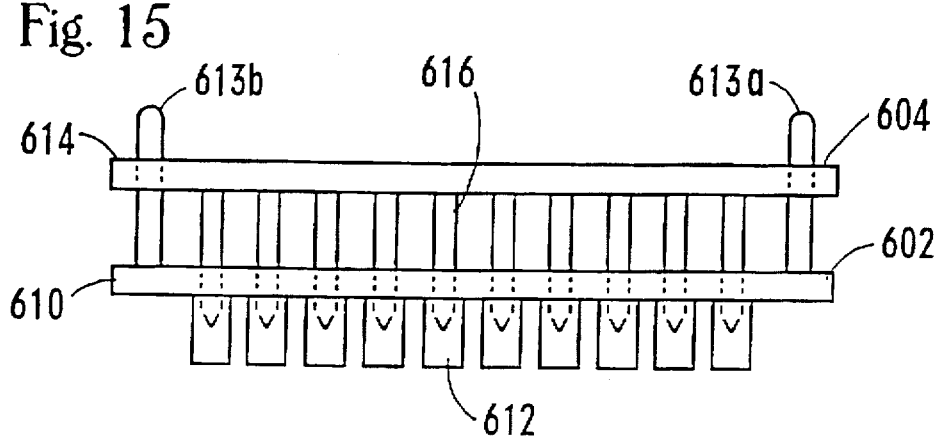
FIG. 15 is a side view illustrating the interengagement of the incision needle plate and incision catheter plate.
Figure 16:
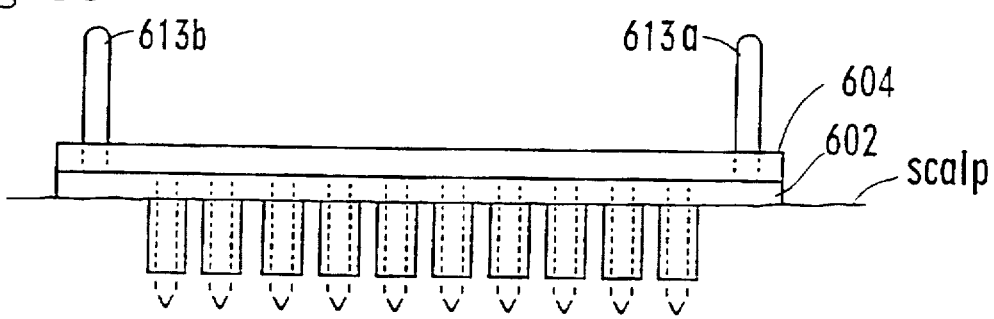
FIG. 16 is a side view illustrating use of the incision needle plate and incision catheter plate for forming multiple cavities in tissue of a patient.

In use, and as illustrated in FIGS. 15 and 16, a user aligns the bores 618a,b of the incision needle plate 604 with the posts 613a,b of the incision catheter plate 602 and presses the two plates together until the base 614 of the incision needle plate 604 is resting on top of the base 610 of the incision catheter plate 602. As illustrated in FIG. 16, when the two plates 602,604 engage one another, the spikes 616 and catheters 612 interengage to form solid "needles" for penetration of the tissue of a patient.

The catheters 612 are each preferably about 5–9 mm, and most preferably about 5–7 mm long, and 1–4 mm in inner diameter. The outer diameter of each spike 616 is preferably nearly equal, but always slightly less than, the inner diameter of each catheter 612. This allows each spike 616 to pass into each catheter 612 and leave little if any space therebetween, whereby tissue can not become entrapped between the interengaging spikes/catheters when they are pushed into the scalp. Further, the lengths of the catheters 612 and spikes 616 are chosen so that their total length is sufficient to create an aperature in the tissue of sufficient depth for proper hair graft placement (normally about 6–8 mm).

Once pressed into the tissue as illustrated in FIG. 16, the incision needle plate 604 is removed. The incision catheter plate 602 remains in place, with the catheters 612 thereof forming apertures in the tissue for placement of hair grafts.

Preferably, the user utilizes the hair graft catheter plate 606 and hair graft needle plate 608 for placement of the hair grafts.

The hair graft catheter plate 606 comprises a base 620 having a number of catheters 622 extending downwardly therefrom. As with the catheters 612 of the incision catheter plate 602, these catheters 622 are preferably hollow, and aligned with passages or bores passing through the base 620. The catheters 622 are arranged on the bottom of the base 620 for engagement with the catheters 612 of the incision catheter plate 602.

Bores 624a,b extend through an extension portion of each end of the base 620. The bores 624a,b are position on the base 620 for alignment with the posts 613a,b of the incision catheter plate 602.

The hair graft needle plate 608 comprises a base 626 having a number of cylindrical, blunt end rods 626 extending downwardly from a bottom surface thereof. The rods 626 are arranged for engagement with the catheters 612,622 of the incision catheter plate 602 and hair graft catheter plate 606, respectively.

Bores 630a,b are located in the base 626 of the plate 608 at extension portions thereof. The bores 630a,b are sized and positioned to allow the posts 613a,b of the incision catheter plate 602 to pass therethrough.

In use, a user loads hair grafts into the catheters 622 of the hair graft 632 catheter plate 606. The user then aligns the bores 624a,b of this plate 606 with the posts 613a,b of the incision catheter plate 602, and presses the hair graft catheter plate 606 downwardly until base 620 thereof engages the base 610 of the incision catheter plate 602 (see FIG. 17).

The catheters 622 of the hair graft catheter plate 606 are sized to slide within the catheters 612 of the incision catheter plate 602. For example, when the inner diameter of each catheter 612 of the incision catheter plate 602 is about 1.7 mm, the outer diameter of each hair graft catheter plate catheters 622 is about 1.2 mm. Further, it is preferred that the hair graft catheter plate catheters 622 extend into the tissue to almost an equal depth of the incision catheter plate catheters 612. To compensate for the thickness of the incision catheter plate base 610, this means the hair graft catheter plate catheters 622 must be slightly longer that the incision catheter plate catheters 612.

Figure 17:
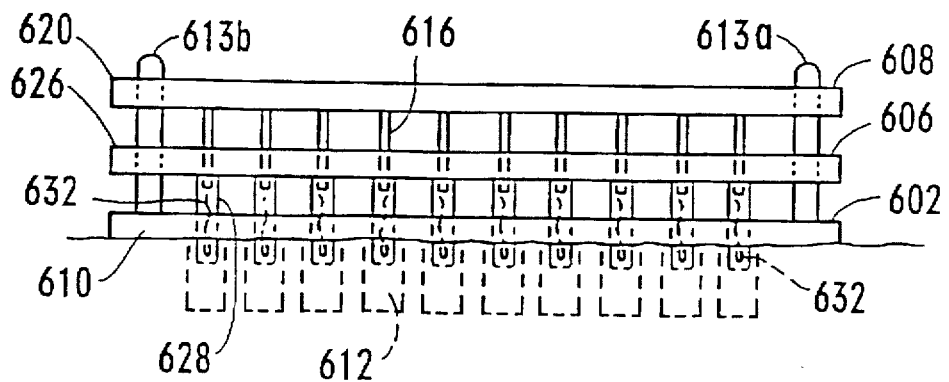
FIG. 17 is a side view illustrating interengagement of the hair graft needle plate, hair graft catheter plate, and incision catheter plate, whereby hair grafts are pressed from the hair graft catheter plate into cavities formed in the tissue.

The user utilizes the hair graft needle plate 608 to press the hair grafts 632 from the catheters 612,622. The user aligns the bores 630a,b of the hair graft needle plate 608 with the posts 613a,b of the incision needle plate 602 and presses the hair graft needle plate 608 downwardly, as illustrated in FIG. 17. Once fully depressed, the user lifts the combined and stacked incision catheter plate 602, hair graft catheter plate 606 and hair graft needle plate 608 from the tissue, leaving the hair grafts 632 implanted in the tissue.

The rods 622 of the hair graft needle plate 608 preferably have an outer diameter which is slightly less than the inner diameter of the hair graft catheter plate catheters 628. The rods 622 are preferably long enough so that they extend to near the bottom of the incision catheter plate catheters 612 when engaged therewith. One of the advantages of using a fourth plate—the hair graft needle plate 608—instead of the three plate arrangement described above is that the lengths of the rods 622 can be chosen so that they do not extend outwardly from the ends of the catheters 612 like would happen if the spikes 616 of the incision needle plate 604 were used for this task. This prevents the user from driving the hair grafts into the tissue of the patient.

Second, the shape of the rods 622 allows for more effective displacement of the grafts from the catheters than when using a pointed spike. Use of the flat ended rod 622 presents less risk of damage to the hair graft.

As with the previously-described form of the invention, the plates may comprise substantially rigid members made of plastic or similar material. In some instances, however, the plates may be constructed of a slightly flexible material so that they can conform to the tissue contour of the patient. The spikes, rods, and catheters, however, are preferably constructed of a rigid material which easily penetrates tissue.

While the spikes, rods, and catheters are illustrated in two rows of spaced-apart members, their location may vary. In particular, the spikes, rods and catheters may be arranged in any variety of patterns for use in locating hair grafts in the same variety of patterns in the scalp.

Advantageously, in this form of the invention, the interengagement of the incision needle plate spikes 616 with the incision catheter plate catheters 612 forms, in essence, a single rigid "needle" for forming an aperture in tissue. This is advantageous over use of a regular dilator or a catheter for several reasons. First, use of a catheter alone may result in tissue being forced into the interior of the catheter, thus blocking hair graft placement. Alternatively, use of a dilator alone can be difficult, because when the dilator is removed, the aperature in the scalp often closes, preventing positioning of the hair graft in the tissue.

Further, in this and the last form of the invention, the catheters or guides and spikes and rods can be located at an angle of other than perpendicular to the base of each respective plate. In this manner, a user can create an aperature in the tissue which lie at an angle other than perpendicular thereto. This is important, for most hair grows naturally from the scalp at other than an angle of perpendicular thereto. Use of template or plates having members extending at an angle of other than perpendicular to the scalp allows placement of hair grafts at a similar angle in the scalp.

Another aspect of the last two forms of the invention which is advantageous is that a hair grafts can be pre-loaded into a number of plates/templates for later use. With several separate plates/templates pre-loaded, a user can very quickly create apertures with the other members and then place large numbers of hair grafts very quickly.

The spikes may have forms other than that described above. In particular, the spikes may have a "body" which is smaller in diameter than the tip. The spikes may also have a tip which comprises a thin blade-like element as opposed to a point. In some instances, it might also be desirable for the spike to be hollow instead of solid.

The wall of the catheter at the end thereof may be tapered or sharp to aid in the insertion of the device into the tissue. Alternatively, instead of the wall of the catheter ending perpendicular to the length of the wall, the end of the catheter may be entirely tapered.

Also, the shapes of the plates (or bases thereof) may vary widely dependent upon the area of tissue in which the grafts are to be planted. For example, the plates may be round, square, or irregular-shaped. The means for aligning the plates may include other types of guides or other similar members known in the art.

Figure 18:
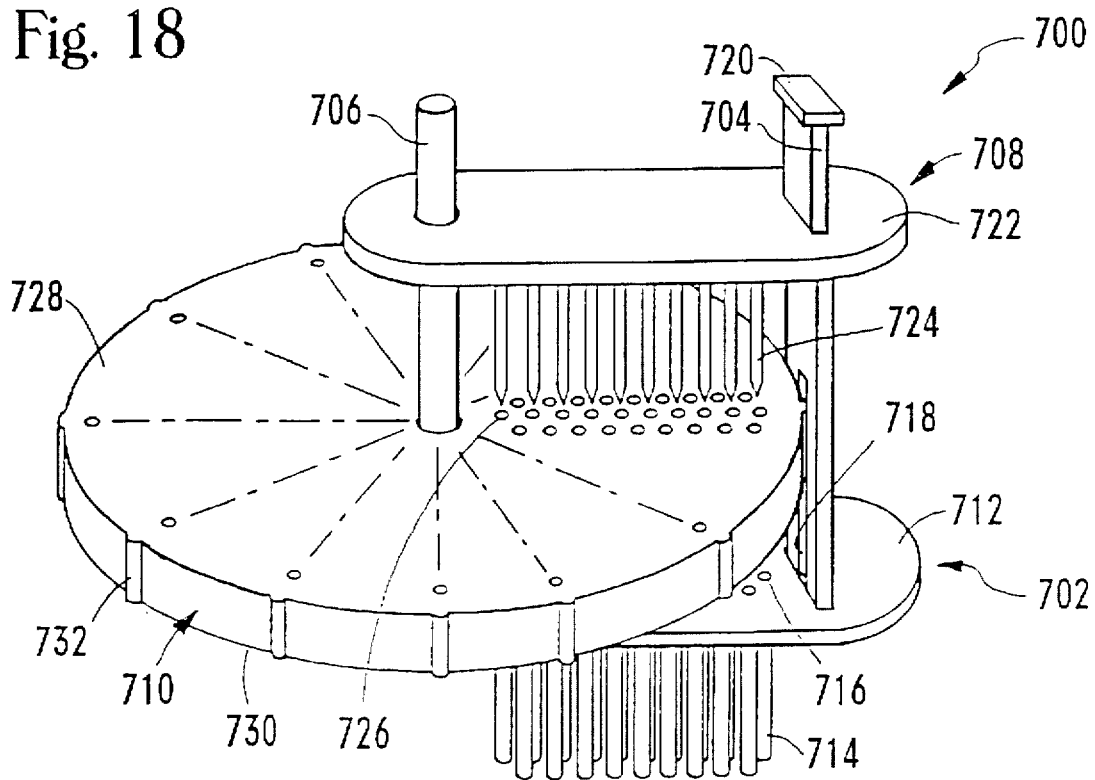
FIG. 18 is a perspective view of a device of the seventh form of the present invention.
Figure 19:
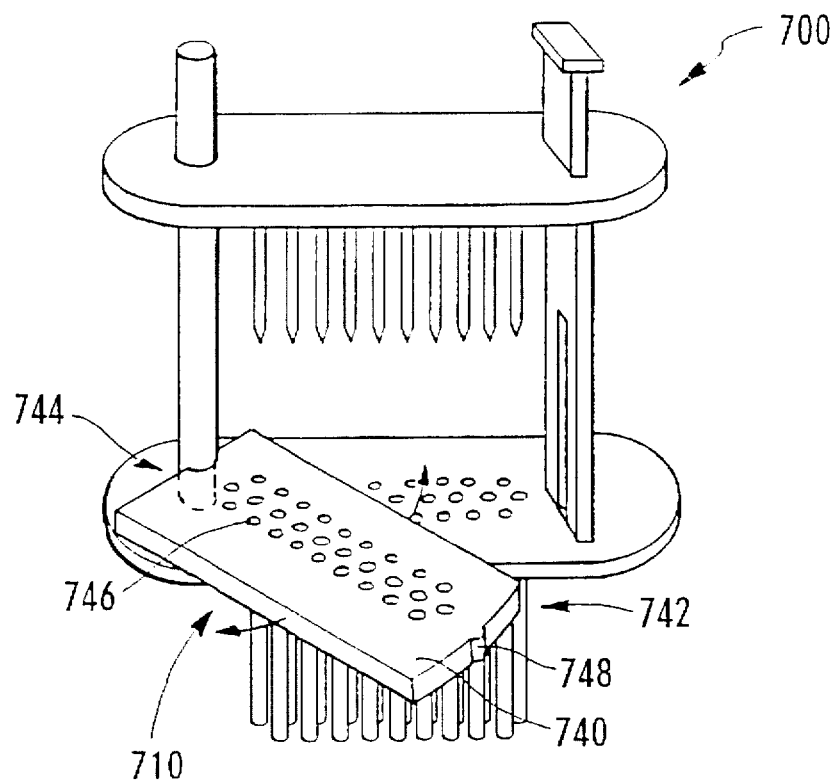
FIG. 19 is a perspective view of an alternative embodiment of the device of the seventh form of the present invention.

Yet another variation of the present invention is illustrated in FIGS. 18–19. In this variation of the invention, the templates or plates of the above-described versions of the invention are "mechanized" for faster graft placement.

The device 700 of this form of the invention comprises a first or lower plate 702 having two upwardly extending guides 704,706, an upper or second plate 708 movably mounted on the guides, and a cartridge 710 located between the upper and lower plates.

The lower plate 704 comprises a base member 712 having a number of hollow catheters 714 extending downwardly therefrom and aligned with bores 716 passing through the base. The catheters 714 are arranged on the base 712 in the same pattern in which hair grafts will ultimately be implanted in the tissue of a patient.

The base 712 is preferably fairly rigid and constructed of a durable, sterilizable material, such as plastic. The base 712 is preferably elongate in shape, having first and second ends located outwardly of the bores 716.

Preferably, means for guiding the upper plate 708 between a first raised and a second lowered position are provided. The means preferably comprises guides 704,706 extending upwardly from the ends of the plate 702.

The first guide 704 is a flat member extending upwardly from its connection to the base 712 of the lower plate 702. The guide 704 is fairly wide to accommodate an indentation 718 therein. A stop 720 is located at an end of the guide 704 located opposite the lower plate 702, for limiting the upward movement of the upper plate 708 thereon.

The second guide 706 is a cylindrical post extending upwardly from the end of the base 712 of the lower plate 702 opposite the first guide 704. Both the first and second guides 704,706 are preferably made of a durable and sterilizable material, and have a length sufficient to allow travel of the upper plate 708 between the positions described below.

The upper plate 708 is preferably shaped similar to the lower plate 702, comprising a base 722 having a number of spikes 724 extending downwardly therefrom. The spikes 724 are cylindrical members having pointed tips which are sized for insertion into the hollow catheters 714 of the lower plate 702. The length of each spike 724 is chosen such that it extends slightly from the end of the catheter 724 when pressed downwardly therethrough as described below.

First and second passages are located in the upper plate 708 for acceptance of the first and second guides 704,706, whereby the upper plate 708 may slide up and down along the guides.

As illustrated in FIG. 18, the cartridge 710 comprises a wheel rotatably mounted on the second guide 706 between the lower and upper plates 702,708. The cartridge 710 preferably has a radius equal to the distance between the first and second guides 704,706.

A number of bores 726 pass through the cartridge 710 from a top surface 728 to a bottom surface 730 thereof. The distance between the top and bottom surfaces 728,730 is great enough that a hair graft may be positioned inside each bore 726. Preferably, the bores 726 are arranged in sets about the cartridge. One set is illustrated in FIG. 18. Other sets of bores 726 (not illustrated) are located about the lines illustrated on the top surface 728 of the cartridge 710.

Each set of bores 726 includes a number of bores equal in number to the spikes 724 and catheters 714, and arranged in the same pattern.

Means for aligning the sets of bores 726 of the cartridge 710 with the spikes 724 and catheters 714 of the plates 702,708 are provided. Preferably, this means comprises a number of beads 732 located on the cartridge 710 and the indentation 718 in the first guide 704.

The beads 732 are located on the outwardly facing surface of the outer edge of the cartridge 710. These beads 732 extend slightly outwardly of the cartridge for engagement with the indentation 718 in the first guide 704. The beads 732 are positioned on the cartridge 710 such that when a bead 732 engages the indentation 718, one of the sets of bores 718 is aligned with the spikes 724 and catheters 714.

Use of this form of the invention is as follows. A user aligns an empty set of bores 726 of the cartridge 710 with the spikes 724 and catheters 714. The user accomplishes this by raising the upper plate 708 along the guides 704,706, and then rotating the cartridge 710 until one of the beads 732 engages the indentation 718.

The user then presses the upper plate 706 downwardly, passing the spikes 724 through the bores 726 in the cartridge and into the catheters 714. At this time, the tips of the spikes 724 protrude slightly from the ends of the catheters 714, such that the spikes and catheters interengage to form "needles." The user then presses the device 700 downwardly so that the spikes 724 and catheters 714 enter the tissue of a patient. The user stops when the lower plate 702 rests on the tissue of the patient.

The user then raises the upper plate 708 until the spikes 724 are located above the cartridge 710. The user rotates the cartridge 710 until a set of bores 726 containing hair grafts is aligned with the spikes 724. The user or another party can load any of the other sets of bores 726 with hair grafts before or during the procedure. In particular, a user places hair grafts into any or all of the bores 726.

Once aligned, the user presses the upper plate 708 downwardly. As the upper plate 708 moves downwardly, the spikes 724 press the hair grafts in the bores 726 down into the catheters 714. The user then raises the upper plate 708 and removes the device 700 from the tissue. A hair graft is left in the tissue of the patient in each spot corresponding to where a catheter 714 penetrated the tissue and a hair graft was pressed therein.

The user then aligns an empty set of bores 726 so that the spikes 708 can be lowered therethrough and used to reinsert the device into the tissue of the patient in a new location.

Advantageously, this device 700 allows a user to preload several sets of bores 726 with hair grafts, whereby the device may be used to place several sets of hair grafts in very quick succession.

As illustrated in FIG. 19, a similar result can be achieved when the cartridge 710 used with the device is not a wheel but comprises a single segment. In this version, a cartridge 740 takes the form of a rectangular segment having a first end 742 and a second end 744. Bores 746 like those described above pass through the cartridge 740.

The first end 742 of the cartridge 740 is designed for engagement with the first guide 704. In particular, the first end 742 of the cartridge 740 preferably includes a bead 748 extending outwardly therefrom for engagement with the indentation 718 in the first guide 704.

The second end 744 of the cartridge 740 is designed for engagement with the second guide 706. Preferably, the second end 744 of the cartridge 740 has a semi-circular cut-out.

In use, the user presses the second end 744 of the cartridge 740 into engagement with the second guide 706. The user rotates the cartridge 740 into place when the bead 748 thereon engages the indentation 718 in the first guide 704.

A user utilizes an empty cartridge 740 when inserting the device 700 into the tissue of a patient. The user utilizes a cartridge 740 having bores filled with hair grafts when ready to insert the grafts.

Advantageously, the user may replace cartridges 740 as needed, and when a user has a number of cartridges 740, several may be pre-loaded with hair grafts for quick placement of large numbers of grafts.

In this form of the present invention, it is also possible for device 700 to be configured for placement of hair grafts at an angle into the tissue. The catheters, spikes and bores may be angled (at other than perpendicular to the plates/cartridge) for placement of the grafts. In that instance, the guides 704,706 should also be angled to permit sliding of the upper plate 708 up and down while the spikes move in and out of the bores/catheters.

It will be understood that the above described arrangements of apparatus and the method therefrom are merely illustrative of applications of the principles of this invention and many other embodiments and modifications may be made without departing from the spirit and scope of the invention as defined in the claims.

I claim:

1. A device for placement of hair grafts in the tissue of a patient, comprising:
    a first plate comprising a base member having a number of first bores passing therethrough and a number of hollow first catheters extending therefrom and aligned with said first bores;
    a second plate comprising a base having a number of first spikes extending therefrom, said spikes arranged and sized for location within said first catheters;
    a third plate having a base with a number of second bores passing therethrough and a number of hollow second catheters extending therefrom and aligned with said second bores, said second catheters sized for location within said first catheters; and
    a fourth plate having a base with a number of second spikes extending therefrom, said second spikes arranged and sized for location within said second catheters.

2. The device of claim 1 further including means on said first plate for aligning said plates for registry of said first spikes within said first catheters and said second spikes within said second catheters.

3. The device of claim 2, wherein said means for aligning comprises two posts extending upwardly from said first plate and two bores located in each of said second, third, and fourth plates for passage of said posts therethrough.

4. A method of locating a plurality of hair grafts in the tissue of a patient, comprising the steps of:
    locating a plurality of spikes extending downwardly from a base member of a first plate into a plurality of hollow guide members extending downwardly from a base member of a second plate;
    pressing said spikes in said guide members into the tissue of the patient;
    removing said first plate from said second plate;
    placing a plurality of hair grafts into the plurality of guide members of said second plate; and
    removing said second plate from the tissue of the patient.

5. The method of claim 4, wherein said placing a plurality of hair grafts into the plurality of guide members comprises the steps of:
    pressing a number of catheters extending downwardly from a third plate into said guide members of said second plate; and
    pressing a number of spikes extending downwardly from a fourth plate into said catheters of said third plate.

6. The method of claim 5, further including the step of locating hair grafts into said catheters of said second plate.

7. A device for placement of a number of hair grafts in tissue of a patient comprising:
    a lower plate having a number of bores therein and a number of hollow catheters extending from said plate and aligned with said bores;
    an upper plate movably mounted to said lower plate, said upper plate having a number of spikes extending therefrom;
    a cartridge located between said upper and lower plates, said cartridge having a set of bores therein corresponding to said spikes in said upper plate.

8. The device of claim 7, wherein further including a pair of guides extending upwardly from said lower plate, said upper plate mounted on said guides.

9. The device of claim 7, wherein said cartridge comprises a wheel rotatably mounted to said lower plate.

10. The device of claim 9, wherein said cartridge includes more than one set of bores.

11. The device of claim 9, wherein said cartridge is rotatably mounted on a post extending upwardly from said lower plate.

12. The device of claim 7, further including means for aligning said bores with said spikes.

13. The device of claim 12, wherein said means for aligning includes at least one bead located on said cartridge.

* * * * *